(12) United States Patent
Inoue et al.

(10) Patent No.: US 6,576,809 B1
(45) Date of Patent: Jun. 10, 2003

(54) DISPOSABLE DIAPER

(75) Inventors: Toshio Inoue, Kagawa-ken (JP); Naoto Ohashi, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 09/547,874

(22) Filed: Apr. 12, 2000

(30) Foreign Application Priority Data

Apr. 13, 1999 (JP) .............................................. 11-105963

(51) Int. Cl.⁷ ................................................ A61F 13/15
(52) U.S. Cl. ........................ 604/361; 604/365; 604/367
(58) Field of Search ................................. 604/361, 362, 604/385.01, 375, 367, 385.22, 385.23

(56) References Cited

U.S. PATENT DOCUMENTS

| | | | | |
|---|---|---|---|---|
| 4,834,733 A | * | 5/1989 | Huntoon et al. | ............ 604/361 |
| 5,364,381 A | * | 11/1994 | Soga et al. | .................. 604/366 |
| 5,503,919 A | * | 4/1996 | Litchholt et al. | ............ 428/101 |
| 5,843,056 A | | 12/1998 | Good et al. | |
| 6,044,515 A | * | 4/2000 | Zygmont | .................... 15/209.1 |
| 6,127,595 A | * | 10/2000 | Makoui et al. | ............. 604/358 |
| 6,140,551 A | * | 10/2000 | Niemeyer et al. | .......... 604/367 |
| 6,394,989 B2 | * | 5/2002 | Mizutani | ..................... 604/383 |

FOREIGN PATENT DOCUMENTS

EP          0 813 850         12/1997

* cited by examiner

Primary Examiner—Aaron J. Lewis
Assistant Examiner—Jamisue Webb
(74) Attorney, Agent, or Firm—Lowe Hauptman Gilman & Berner, LLP

(57) ABSTRACT

A backsheet of a disposable diaper comprises a stretched plastic film containing grains of inorganic filler wherein the backsheet presents surfaces roughed by the presence of the grains and has a moisture permeability of 800–3000 g/m²·24 hr and a total light transmissivity of 60–85%.

5 Claims, 5 Drawing Sheets

DISPOSABLE DIAPER

BACKGROUND OF THE INVENTION

This invention relates to a disposable diaper and more particularly to such a diaper improved so that occurrence of urination can be visually recognized as soon as possible from the outside of the diaper.

Japanese Patent Application Disclosure No. 1993-200063 describes a breathable liquid-impervious sheet used as a backsheet in a disposable diaper. This sheet comprises an polyolefine plastic sheet containing grains of inorganic filler. The sheet presenting surfaces made rough by the presence of the grains is heat-embossed so that the heat-embossed regions may be smoothed. The smoothed regions of the sheet exhibit a sufficiently high light transmissivity to facilitate an absorbent pad wetted with urine to be visually recognized from the outside of the backsheet. Regions remaining rough, on the other hand, exhibit a poor light transmissivity and does not contribute to visual recognition of urination. These rough regions rather contribute to concealment of the stained absorbent pad.

The sheet of prior art having both the high light transmissivity and the concealing property must be subjected to a step of heat-embossing in addition to a step of sheet extrusion. With a consequence, a manufacturing cost may correspondingly increase.

SUMMARY OF THE INVENTION

It is an object of this invention to improve the backsheet used in the disposable diaper having both the high light transmissivity and the concealing property so as to be supplied at a low cost.

According to this invention, there is provided a disposable diaper comprising a liquid-pervious topsheet, a breathable liquid-impervious backsheet and a liquid-absorbent core disposed between these two sheets, wherein: the backsheet is made of a stretched plastic film containing grains of inorganic filler, the backsheet presents surfaces roughed by the presence of the grains and has a moisture permeability of 800–3000 g/m$^2$·24 hr and a total light transmissivity of 60–85%.

This invention includes preferred embodiments as will be described:

The backsheet is bonded to the core by means of hot melt adhesive agent to ensure that a situation in which the core has been wetted with urine can be visually recognized from the outside of the backsheet more easily in regions of the hot melt adhesive agent than in the remaining regions.

Regions of the backsheet having been applied with the hot melt adhesive agent are substantially smoother than the remaining regions.

DETAILED DESCRIPTION OF THE PREFERRED EMBODIMENT

The invention will be more fully understood from the description given hereunder with reference to the accompanying drawings.

Figure 1:
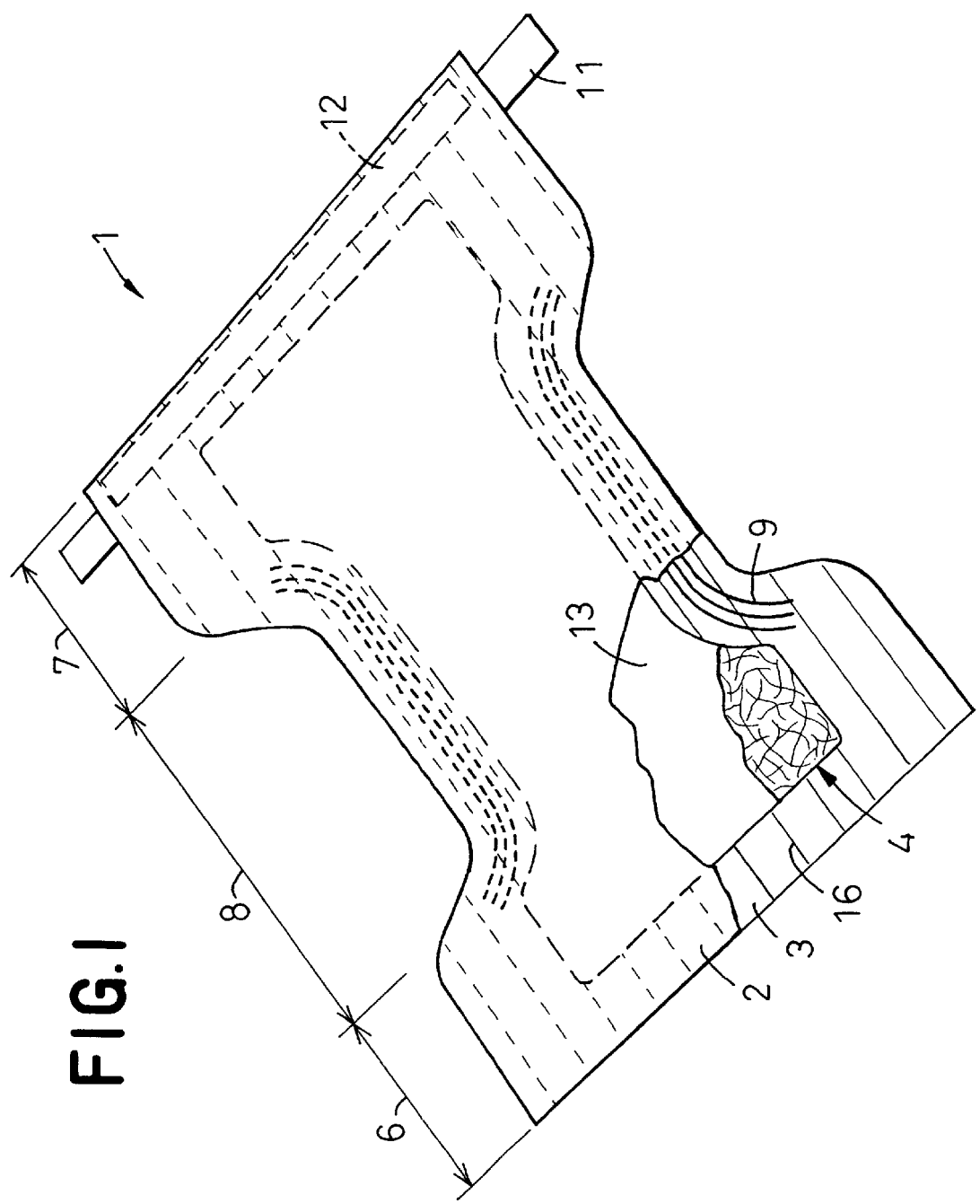
FIG. 1 is a partially cutaway perspective view showing a diaper according to this invention.

A disposable diaper 1 shown by FIG. 1 in a partially cutaway perspective view comprises a liquid-pervious topsheet, a breathable liquid-impervious backsheet 3 and a liquid-absorbent core 4 disposed between these two sheets 2, 3 wherein the two sheets 2, 3 are bonded by means of hot melt adhesive agent 16 to each other along their portions extending outward beyond a peripheral edge of the core 4. Longitudinally of the diaper 1, front and rear waist regions 6, 7 and a crotch region 8 extending between these two waist regions 6, 7 region 8, transversely opposite side edges of the diaper 1 are curved inward and these curved side edges are provided with elastic members 9 destined to be associated with leg-openings secured under tension thereto. A pair of tape fasteners 11 extend laterally from transversely opposite side edges of the rear waist region 7. The rear waist region 7 is provided along its longitudinal end with an elastic member 12 destined to be associated with a waist-opening. The elastic members 9, 12 are disposed between the topsheet 2 and the backsheet 3 and secured under tension to the inner surface of at least one of the topsheet 2 and the backsheet 3.

The topsheet 2 is made of a nonwoven fabric or porous plastic sheet and preferably has a moisture resistance of 0–200 mm as measured according to JIS-L-1092, a testing method of which will be described hereinafter.

The backsheet 3 is made of a mono- or biaxially oriented plastic film, for example, a polyolefine based film containing grains of suitable inorganic filler such as calcium carbonate or barium sulfate. The backsheet 3 has a breathability of 800–3000 g/m2·24 hr as represented by a corresponding moisture permeability as measured in accordance with JIS-Z-0208, a testing method of which will be described hereinafter. The backsheet 3 has a total light transmissvity of 65–85% as measured in accordance with JIS-K-7105, a testing method of which will be described hereinafter.

The core 4 comprises a mixture of fluff pulp and superabsorptive polymer particles molded in an hourglass-shape and then covered with tissue paper 13.

Figure 2:
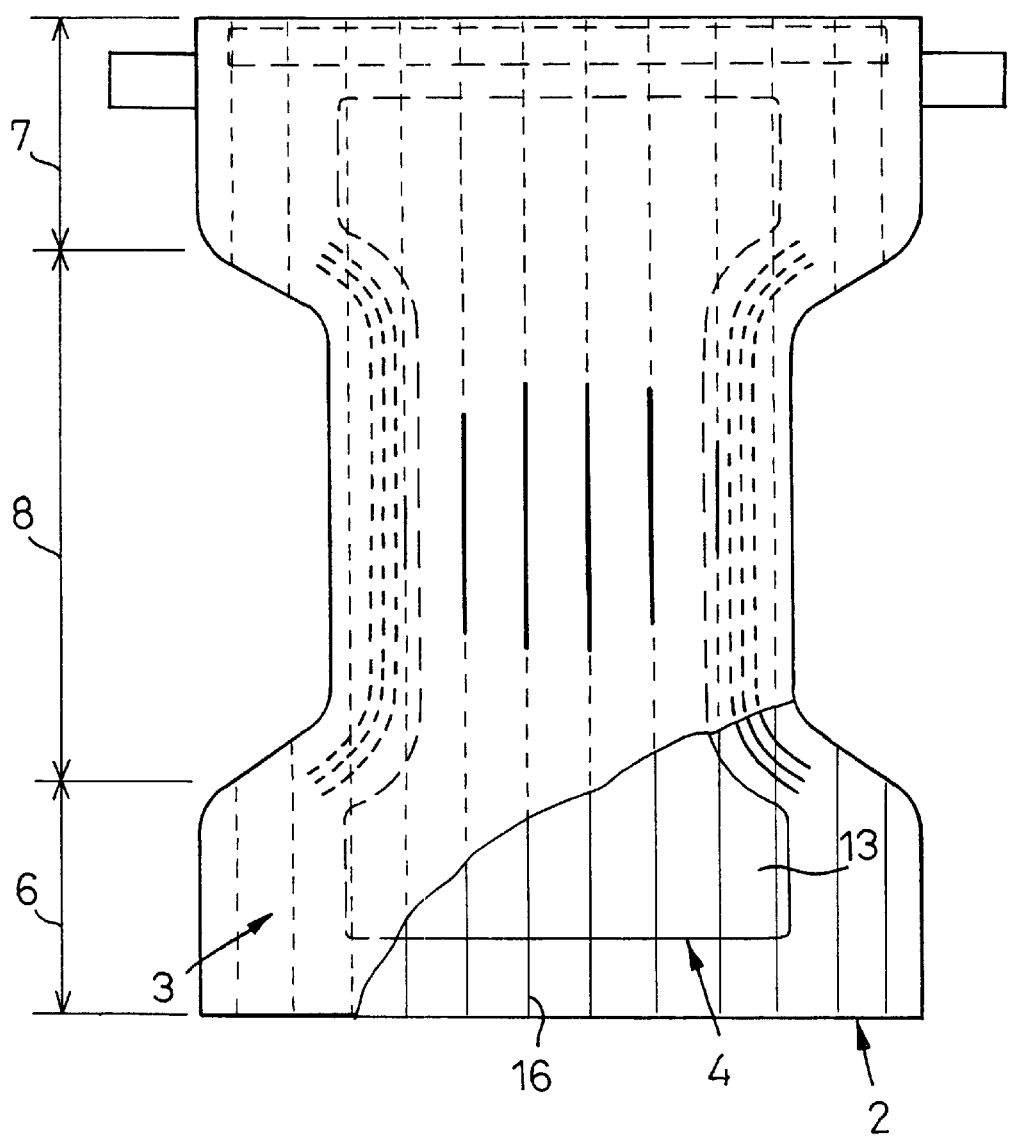
FIG. 2 is a plan view showing the diaper as viewed from the side of a backsheet and as partially broken away.

FIG. 2 is a partially cutaway plan view showing the diaper 1 as viewed from outside of the backsheet 3. The crotch region 8 is illustrated to be in a state enabling occurrence of urination to be visually recognized from the outside of the backsheet. The backsheet 3 is bonded to the tissue paper 13 covering the core 4 and the topsheet 2 by means of hot melt adhesive agent 16 applied to the backsheet 3 to form a plurality of straight stripes extending longitudinally of the backsheet 3. In the crotch region 8, the tissue paper 13 is wetted with urine discharged on the diaper 1 and this situation can be visually recognized from outside of the backsheet 3. Particularly in the stripe-like regions along which the backsheet 3 is in close contact with the tissue paper 13, the occurrence of urination distinctly appear in the form of plural lines as shown. The backsheet 3 has rough surfaces and such roughness substantially disappears in the regions of the hot melt adhesive agent 16. As a result, light diffusion significantly decreases in the regions which enables then the occurrence of urination to be visually recognized. It should be understood here that such effect of the hot melt adhesive agent can be obtained only when the moisture permeability and the total light transmissivity of the backsheet 3 are in the ranges, respectively. To make the effect more reliable, it is desirable to bind the hot melt adhesive agent and the backsheet 3 together when the hot melt adhesive agent is at a proper temperature to soften or slightly melt the backsheet 3.

It is possible without departing from the scope of the invention to apply the hot melt adhesive agent 16 in an appropriate pattern other than the rectilinear pattern as shown, for example, a spiral pattern.

With the disposable diaper as has been described hereinabove, it is unnecessary to subject the breathable liquid-impervious backsheet to any additional treatment such as the heat-embossing in other that the occurrence of urination can be visually recognized from the outside of the backsheet. Accordingly, the disposable diaper's backsheet according to this invention can be made at a low cost and the diaper can be supplied at a correspondingly low price.

Figure 3:
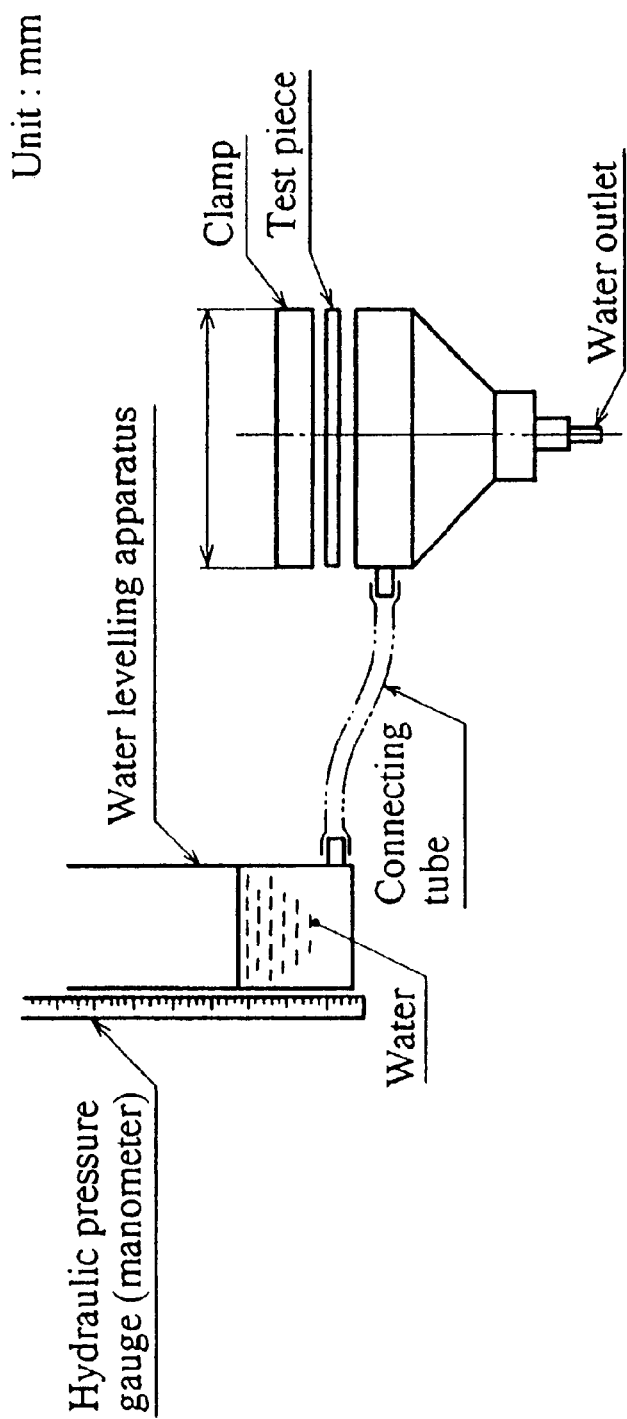
FIG. 3 is a schematic view of a testing device used in JIS-L-1092.

In the following section, a testing method in accordance with JIS-L-1092 will be described with reference to FIG. 3.

Method A (Low hydraulic pressure method) is as follows:

1) Apparatus and material. The following apparatus and material shall be used:

1.1) Water penetration test apparatus (for low hydraulic pressure). The apparatus shown in FIG. 3 or those equivalent thereto whose rate of increase of water pressure is (60±3) cm/min and (10±0.5) cm/min. The clamp shall be of such size that he part of the test specimen which touches the water is 100 cm 2.

1.2) Hydraulic pressure gauge (manometer). With 0.5 cm scale and of approximately 1 m or higher in the maximum water level when raising the water levelling apparatus.

1.3) Water. The distilled or ion-exchange water maintained at (20±2) ° C. in the test shall be used and chosen alternative shall be stated in the test report. (Informatiave reference: Water temperature influences sometimes the test result).

Procedure. From the test specimens specified in 5, sample test pieces each measuring approximately 15 cm×15 cm, take five sheets of them for the following each test, mount the test pieces on the water penetration test apparatus shown in FIG. 2 in such a way that the front surface touches the water, raise the water level by raising the water levelling apparatus containing water at a speed of (60±3) cm/min or (10±0.5) cm/min and measure the water level to an accuracy of cm at the time when the water comes out from the places on the reverse surface of the test pieces. Note: The front surface is the waterproofed surface or the surface the water touches at the time of use. (Informative reference: The test for water penetration, method A (Low hydraulic pressure method) is the same test method as that in ISO 811).

The accuracy of the water level to be reported is:

less then 1 m: 0.5 cm from 1 m and less than 2 m: 1.0 cm 2 m or more:2.0 cm

Each result of five test pieces and the average value shall be expressed down to first decimal place. If the water does not come out from the three places even when the water level is raised, measure the water level at the time when the water comes out from one or two places and state that effect in the test report.

The extremely small water drops which do not grow after being formed and the waterdrops formed by penetrating through the same place shall be ignored.

In the following section, a testing method in accordance with JIS-Z-0208 will be described with reference to FIG. 3.

Testing Methods for Determination of the Water Vapour Transmission Rate of Moisture-Proof Packaging Materials (Dish Method)

Scope—This Japanese Industrial Standard specified the method using the water vapour transmission dish for testing the water vapour transmission rate of the moisture-proof packaging materials such as plastic film converted paper and the like.

Definition—The water vapour transmission rate is the quantity of vapour passing through the unit are of filmy substance for the definite hour. In this standard, when constituting the boundary surface by the moisture-proof packaging materials at the temperature of 25° C. or 40° C., and keeping the air of one side at a relative humidity of 90% and the air of the other side at the dry state by moisture absorbent, the value having converted the mass (g) passing through this boundary surface for 24 h into the value per 1 $m^2$ shall be defined as the water vapour transmission rate.

Because the affects of temperature and humidity on the water vapour transmission rate are not simple, the rate having been estimated from the measured value under the temperature and the humidity condition different from the testing condition as specified in this standard cannot be regarded as the water vapour transmission rate termed in this standard.

Apparatus

Figure 4:
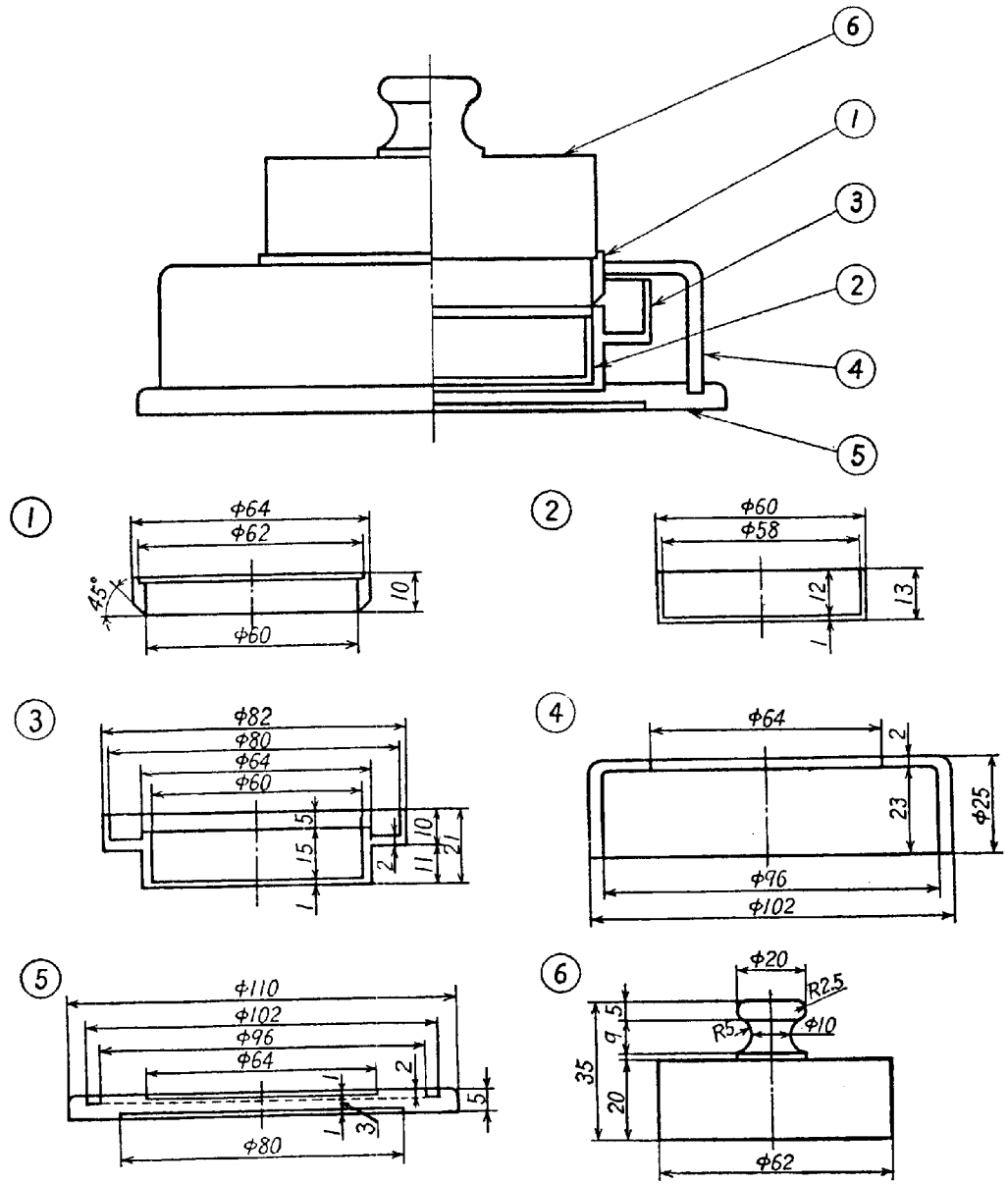
FIG. 4 is a schematic view of a testing device used in JIS-Z-0208.

Water Vapour Transmission Dish. The water vapour transmission dish, hereinafter referred to as the "dish", shall meet the following conditions. An example of the dish and its accessories is shown in FIG. 4.

1) The area of water vapour transmission shall be not less than 25 cm2 and be capable of specifying its area clearly. The area of water vapour transmission shall be calculated from the inner diameter of the ring.

2) The quality of material shall have no permeability for the vapour and produce no corrosion and the like under the testing condtion.

3) The dish shall have enough rigidity not to be transformed during operation.

4) The peripheral part of test piece shall be sealed completely.

Cover—Where the use of cover is required (see (10) under Operation, its cover shall be one capable of covering the one side of test piece completely and it is advisable that is material is same as that of cup.

Thermo-Hygrostat—The thermo-hygrostate shall be one in which the air kep at the specified temperature and humidity can circulate at a velosity of 0.5 to 2.5 m/s above the test piece. The temperature and humidity conditions at the time of test shall be as follows:

Condition A Temperature: 25±0.5° C. Relative Humidity: 90±2%

Condition B Temperature: 40±0.5° C. Relative Humidity: 90±2%

Chemical Balance. The chemical balance shall be capable of weighing the mass of up to 0.1 mg.

Chemical Agents 4.1 Moisture Absorbent. The moisture absorbent shall be as specified in JIS K 8123. The absorbent having a grain size passing through the sieve of nominal size 2380 $\mu$m as specified in JIS Z 8801 and remaining on the 590 $\mu$m sieve shall be used.

4.2 Sealing Waxes. Use the sealing waxes meeting the following conditions. Further, it is preferable that the filler and the insoluble solid component are not included.

1) It shall be difficult to be peeled off and easy to be operated to seal with wax.

2) It shall be not fragile at room temperature and have no water absorption, nor hygroscopic property, nor fear of oxidation.

3) It is required that the sealing waxes are not softened and deformed when being exposed under the temperature and humidity condition B and the change in the mass of not less than 1 mg in 24 h is not produced, where its exposed surface area is 50 cm².

The following are examples of compounding (in mass ratio) of sealing waxes.

(a) Microcrystalline wax 60% and refined crystal parrafin wax 40%.

(b) Parrafin wax 80% having a melting point of 50 to 52° C. and viscous polyisobutylene (one having a low polymerization) 20%.

(c) Mixture of waxes having oil of 1.5 to 3% at a melting point of 60 to 75° C.

Test Piece—Take the test piece with sufficient cares to represent its sample, cut off not less than three test pieces, which have circular shape having a diameter larger by about 10 μm than the inner diameter of the cup to be used, from the same sample to offer the test.

Where the discrimination of the both top and bottom sides of test specimen is clear, the direction of the side of test pieces can be kept constant according to the use of that material when fitting the test piece with the cup. When measuring on the both sides, prepare not less than three test pieced on each side.

Operation—Where the cup as shown in FIG. 4 is used, fit the test piece with the cup by the following operation and carry out the test. Where other cup is used, carr out the test operation corresponding thereto.

1) Cleanse the cup and after having dried it, warm it up to a temperature of about 30 to 40° C.

2) Put the dish containing moisture absorbent in the cup and place it on the cup base kept horizontally. At this time, keep the surface of moisture absorbent horizontally as far as possible so that the distance from the underside of test piece will become about 3 mm.

3) Put the test piece on the position to become concentric with the cup.

4) Cover the guide to fit with the groove of cup base.

5) Push the ring in as shown in FIG. 4 until the test piece will contact closely with the upper edge of cup to fit the guide and put the weight on it.

6) Draw the guide perpendicularly up with cares not to move the ring to remove it.

7) While rotating the cup horizontally, flow the melted sealing waxes into the groove at the peripheral part of the cup and seal the edge of the test piece. The temperature of melted sealing wax shall not be the temperature likely to impair the measurement such as the part corresponding to the water vapour transmission area will melt or shrink. At this time, take care not to produce cracks, bubbles and others.

8) Remove the weight and the cup base after the sealing waxes have been solidified. Clean the sealing waxes that have been stuck to the part except the sealing part (sides and bottom of the cup and others) by the cloth with a suitable solvent soaked to remove and take as test specimen.

9) Put the test specimen in the thermo-hygrostat kept at the specified test condition.

10) After having placed the test specimen in the thermo-hygrostat not less than 16 h, take it out of the apparatus, let it keep balance with room temperature and measure the mass by the chemical balance. Where the side exposed to the outside of the test place is the material having a large hygroscopic property, cover the test specimen immediately after taking it out of the thermo-hygrostat apparatus to lessen the change of moisture content as far as possible. Where the test piece includes materials such as paper, paper-boards cellophane and the like has been exposed to the other direction, the use of cover is required.

11) Put the test specimen in the thermo-hygrostat again, take the cup out at a suitable time interval, repeat the weighing operation and measure the increase of the mass of cup. Obtain the mass increases per unit hour of consecutive two weighings respectively, continue this test until it will become constant within 5%.

The time interval of the weighings shall be 24, 28 or 96 h and its increase in mass shall be at least not less than 5 mg.

Moreover, it is necessary to compete the test before the moisture absorbent put in the cup has absorbed a moisture of 10% to its mass.

12) Where the water vapour transmission rate of sample is small or where the sample has a hygroscopic property, produce not less than two blank cups without the moisture absorbent by the same operation, add this to the test specimens to conduct the test similarly and it is desirable to correct the increased mass of test specimen at each time interval by the mean value of the mass change of the blank cup.

Calculation—Obtain the water vapour transmission rate from the following formula on each test specimen and round off it to two significant figures as specified in JIS Z 8401.

Water vapour transmission rate $$(g/m^2 \cdot 24h) = \frac{240 \times m}{t \cdot s}$$

where s: area of the water vapour transmission (cm²)

t: total of time intervals between the last two weighings (h)

m: total of increased masses between the last two weighings (mg)

Figure 5A:
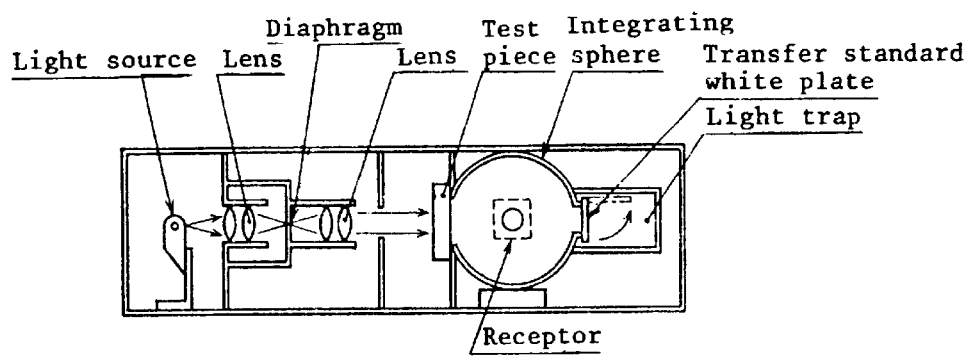
FIG. 5 is a schematic view of a testing device used in JIS-K-7105.
Figure 5B:
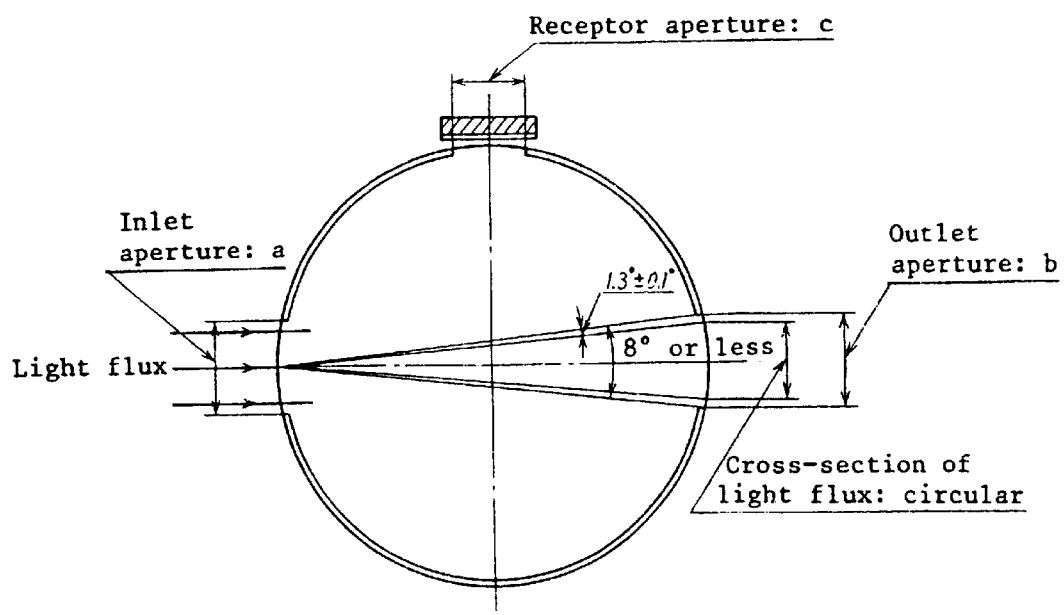

In the following section, a testing method in accordance with JIS-K-7105 will be described with reference to FIGS. 5A and 5B.

Measuring Method A—Measurement shall be performed as follows:

Apparatus—the principle of the optical system of the integrating sphere type light transmittance measuring apparatus is shown in FIG. 5. The apparatus shall meet the optical conditions shown in Table 1.

TABLE 1

Optical Conditions of Apparatus (Measuring Method A)

| Item | Conditions |
|---|---|
| Integrating sphere | The sum of the areas (a + b + c) of the inlet and outlet (the portions where the test piece and the transfer standard white plate are fitted) shall be 4% or less of the total inner surface area of the sphere (see FIG. 5B).<br>The center lines of the outlet and inlet shall be on the same large circle of the sphere and the angle formed by the diameter of the outlet and the center of the inlet shall be 8 degrees or less. |
| Reflecting surface | The transfer standard white plate shall have a uniform high reflectance for all the wave length of visible light. Magnesium oxide, barium sulfate, aluminum oxide and the like are suitable for this purpose.<br>The inner wall of the integrating sphere shall be coated with a material having the same reflectance as the transfer standard white plate. |

TABLE 1-continued

Optical Conditions of Apparatus (Measuring Method A)

| Item | Conditions |
|---|---|
| Light flux | The light flux which illuminates the specimen shall almost consist of parallel rays and shall not include light beams deviating by 3 degrees or more from the optical axis. The center of the light flux shall agree with the center of the outlet. The cross-section of the light flux at the outlet shall be circular and distinct. Further, the angle which is formed by the diameter of the light flux at the outlet referring to the center of the inlet shall be made smaller by 1.3 ± 0.1 degrees than the angle which is formed by the radius of the outlet. The cross-section of the light flux at the outlet of the integrating sphere shall be as shown in FIG. 5B. |
| Light trap | The light trap, when no test piece or not transfer standard white plate is fitted, shall completely absorb light. |
| Light source | The synthetic light A shall be used as the light source. |
| Receptor | The synthetic sensitivity of the receptor shall satisfy the value of Y of the Luther condition for the standard light C by the use of a visual filter. However, where particularly specified, measurement may be performed by using a device which satisfies the value of Y of the Luther condition for the standard light A. |

Test Piece—The test piece used shall be as follows:
(a) The dimensions of the test piece shall be 50 mm×50 mm, and the thickness shall be the original thickness.
(b) The number of test pieces used shall be 3.

Measuring Method—The measurement shall be performed according to the following procedures:
(a) Fit a transfer standard white plate, adjust the indicator of the apparatus at 100 ($T_1$), and adjust the quantity of the incident light.
(b) With the transfer standard white plate fitted, attach the test piece, and measure the quantity of scattering light of the apparatus ($T_2$).
(c) Detach the transfer standard white plate and test piece, attach a light trap, and measure the quantity of scattering light of the apparatus ($T_3$).
(d) With the light trap attached, attach the test piece, and measure the quantity of scattered light produced by the apparatus and test piece ($T_4$).

Method of Calculation—The total light transmittance, diffuse transmittance, and parallel light transmittance shall be calculated from the following formulas:

$$T_1 = T_2$$

$$T_d = T_4 - T_3 \left( \frac{T_2}{100} \right)$$

$$T_p = T_1 - T_d$$

where $T_1$: total light transmittance (%)
$T_d$: diffuse transmittance (%)
$T_p$: parrallel light transmittance (%)

What is claimed is:

1. A disposable diaper, comprising:
   a liquid-pervious topsheet;
   a breathable liquid-impervious backsheet;
   a liquid-absorbent core disposed between the topsheet and backsheet;
   said backsheet being made of a stretched plastic film containing grains of inorganic filler, said backsheet presenting surfaces roughed by the presence of said grains and having a moisture permeability of from about 800 to about 3000 g/m2·24 hr and a total light transmissivity of from about 60 to about 85%.

2. The disposable diaper according to claim 1, wherein said backsheet is bonded to said core by means of a hot melt adhesive agent to ensure that when said core is wetted with urine, said core can be visually recognized from the outside of said backsheet more easily in regions of said hot melt adhesive agent than in remaining regions where said backsheet is not bonded to said core by said hot melt adhesive agent.

3. The disposable diaper according to claim 2, wherein the regions of said backsheet with said hot melt adhesive agent are substantially smoother than the remaining regions.

4. The disposable diaper according to claim 2, wherein said core is bonded to said backsheet when said hot melt adhesive agent is at a temperature sufficient to soften said backsheet.

5. The disposable diaper according to claim 2, wherein said core is bonded to said backsheet when said hot melt adhesive agent is at a temperature sufficient to slightly melt said backsheet.

* * * * *